United States Patent
Anno et al.

(10) Patent No.: US 7,122,213 B2
(45) Date of Patent: Oct. 17, 2006

(54) SUPPLEMENT FOODS AND PHARMACEUTICALS

(75) Inventors: Takahiko Anno, Otsu (JP); Yasuo Kosaka, Matsudo (JP); Tsutomu Yae, Tokyo (JP); Yoshimi Saito, Tokyo (JP)

(73) Assignees: Ryusendo Co. Ltd., Tokyo (JP); V-Tec Co., Ltd., Kanagawa (JP)

( * ) Notice: Subject to any disclaimer, the term of this patent is extended or adjusted under 35 U.S.C. 154(b) by 0 days.

(21) Appl. No.: 10/978,718

(22) Filed: Nov. 1, 2004

(65) Prior Publication Data

US 2005/0196474 A1 Sep. 8, 2005

(30) Foreign Application Priority Data

Mar. 3, 2004 (JP) ............................. 2004-058837

(51) Int. Cl.
*A01N 65/00* (2006.01)
*A61K 47/00* (2006.01)

(52) U.S. Cl. ............... 424/758; 424/754; 424/439; 514/866

(58) Field of Classification Search ........... 424/758, 424/754, 439; 514/866
See application file for complete search history.

(56) References Cited

FOREIGN PATENT DOCUMENTS

| CN | 1168237 A | * | 12/1997 |
| CN | 1077408 C | * | 1/2002 |
| CN | 1437898 A | * | 8/2003 |
| JP | 54014564 A | * | 2/1979 |
| JP | 54028871 A | * | 3/1979 |
| KR | 2002088332 A | * | 11/2002 |

OTHER PUBLICATIONS

Acosta-Patino, J. L. et al., Journal of Ethnopharmacology, 77(1): 99-101, (Sep. 2001), Hypoglycemic action of *Curcubita ficifolia* on type 2 diabetic patients with moderately high blood glucose levels.*

* cited by examiner

*Primary Examiner*—Michele Flood
(74) *Attorney, Agent, or Firm*—Price, Heneveld, Cooper, DeWitt & Litton, LLP

(57) ABSTRACT

The present invention provides effective supplement foods and safe pharmaceuticals, each having a hypotensive effect and anti-diabetic effect and no adverse effects. The supplement foods and pharmaceuticals of the present invention comprise squash extract mixed with onion extract. Synergistic effect of the two extracts can be expected by mixing the onion extract with the squash extract.

2 Claims, 4 Drawing Sheets

FIG. 2
CHANGES OF SUBSTANCES RELATED
TO ELEVATION IN BLOOD PRESSURE
AND HYPOTENSIVE MINERALS AFTER THE INGESTION
OF THE PRODUCTS OF SQUASH EXTRACT MIXED
WITH ONION EXTRACT
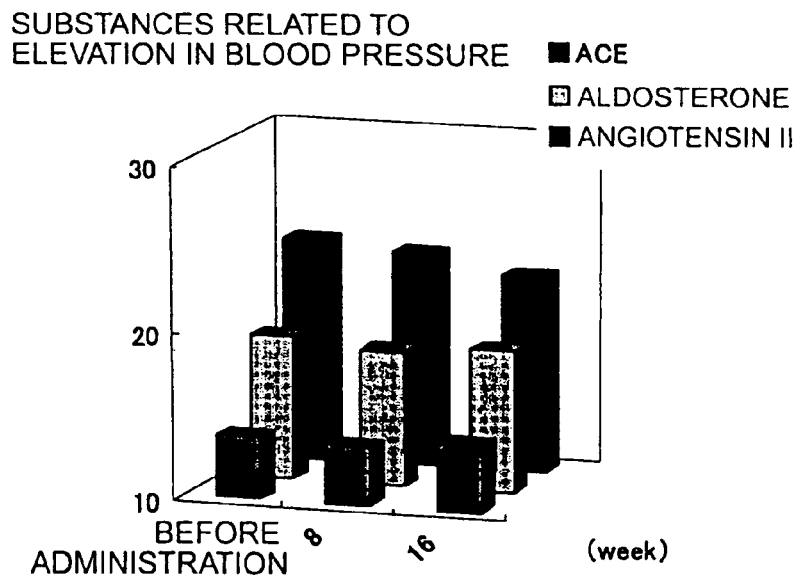
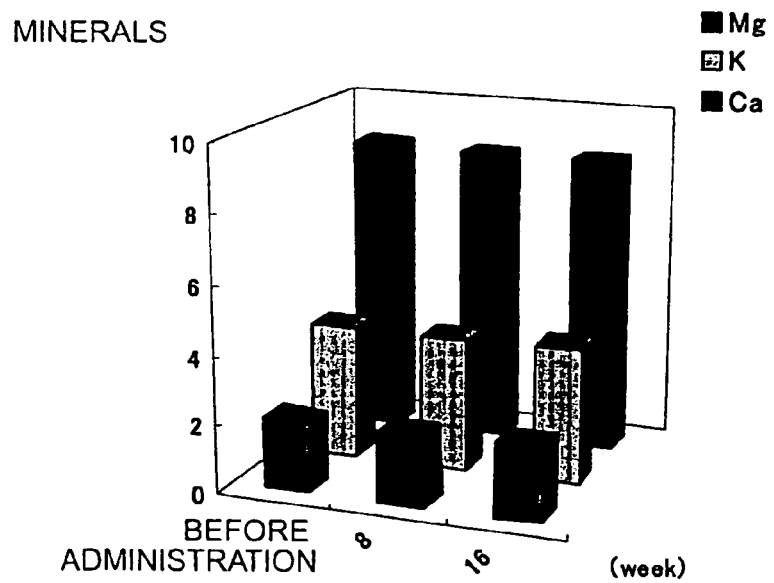

FIG. 3
CORRELATION BETWEEN SYSTOLIC BLOOD PRESSURE AND SUBSTANCES RELATED TO ELEVATION IN BLOOD PRESSURE
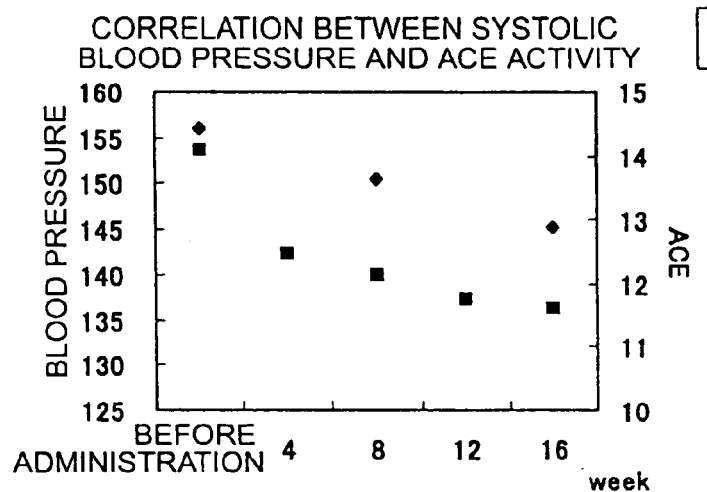
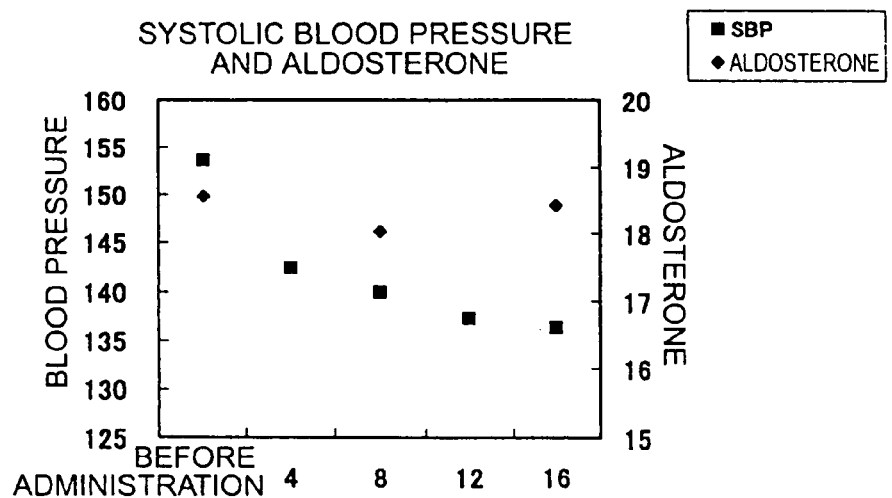
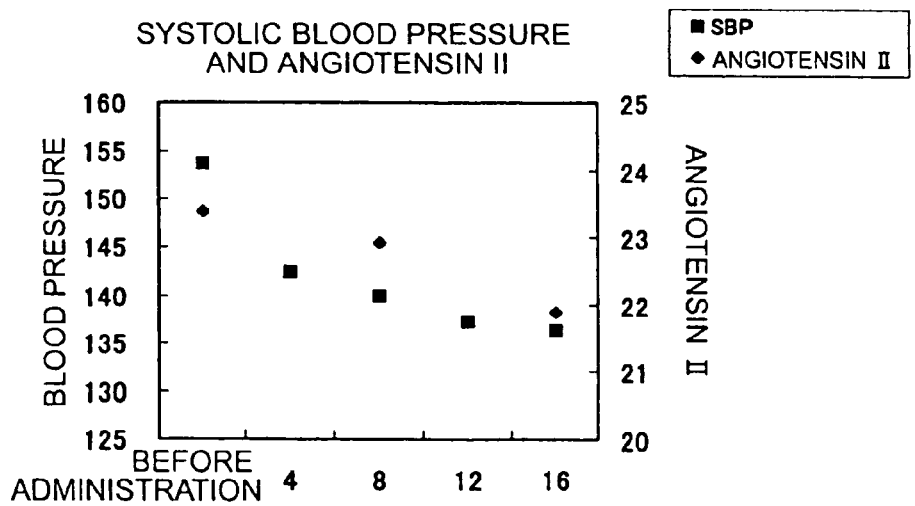

FIG. 4
CHANGES OF 2 HOUR POSTPRANDIAL BLOOD GLUCOSE LEVELS AND $Hb_{A1C}$ AFTER THE INGESTION OF THE PRODUCTS MIXED WITH SQUASH EXTRACT AND ONION EXTRACT
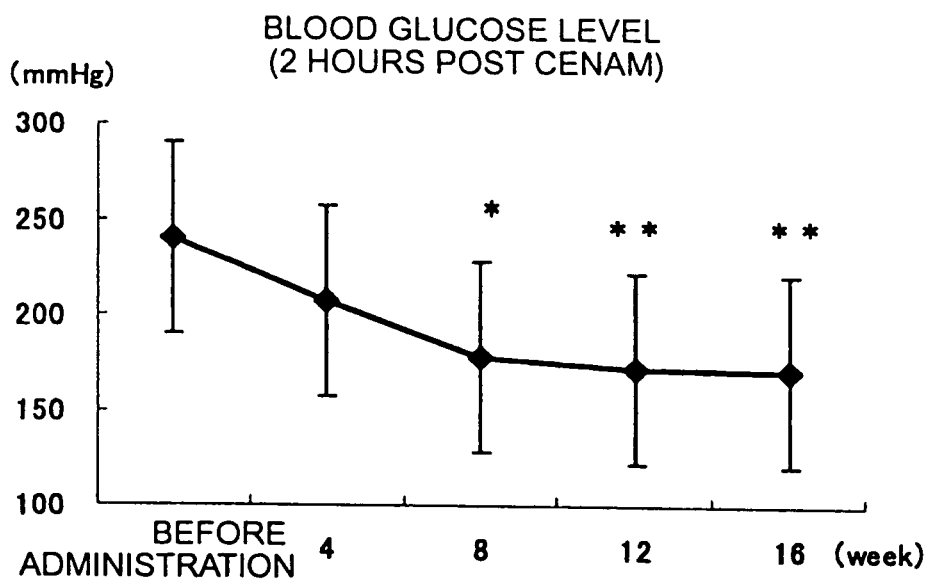
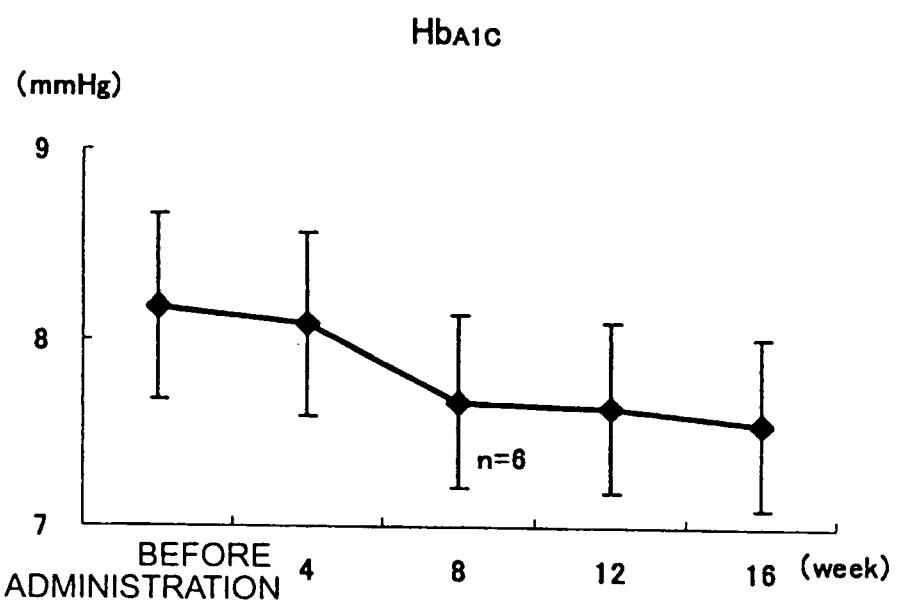
EVALUATED BY T-TEST WITH LEVELS BEFORE ADMINISTRATION AS CONTROL
\*     $p<0.05$
\*\*   $p<0.01$

SUPPLEMENT FOODS AND PHARMACEUTICALS

BACKGROUND OF THE INVENTION

1. Field of the Invention

The present invention relates to supplement foods and pharmaceuticals composed of squash extract mixed with onion extract.

2. Description of the Related Art

It has been conventionally known that onion extract has an anti-diabetic effect (see Japanese Patent Laid-Open No. 10-77232); Yoshimi Saitou, *Effects of Onion Concentrated Dried Tablets* (OCDT) *on Postprandial Hyperglycemiain Diabetic Cases*, Rinsho Iyaku (Clinical Medicines), Vol. 17 No. 7, 1089–1095 (2001); Yoshimi Saitou, *Effects of Onion Concentrated Dried Tablets (OCDT) on Hyperlipidemia in Diabetic Cases*, Rinsho Iyaku (Clinical Medicines), Vol. 17 No. 8, 1216–1221 (2001); Kazuhiko Yoshizawa, Yoshitaka Aiso, *Clinical Effect of Tamaekisu on Type II Diabetics*, Japan Diabetic Society Kanto-Koshinetsu District 41st Lecture Abstract, p.36 (2004)). It is also known that onion extract has a hypotensive effect (see, for example, Yoshimi Saitou, *Effects of Onion Concentrated Dried Tablets (OCDT) on Postprandial Hyperglycemia in Diabetic Cases*, Rinsho Iyaku (Clinical Medicines), Vol. 17 No.7, 1089–1095 (2001)). The hypotensive effect of squash extract is based on its angiotensin converting enzyme inhibitory effect (ACE inhibitory effect). This was discovered by Abe and Kosaka among the inventors, and filed by the applicants (Japanese Patent Application No. 2002-312459).

Hypotensive agents having an ACE inhibitory effect (for example, calcium antagonists) have actions, which include actions of suppressing the new onset of diabetes, and actions of suppressing the onset of complications in diabetic patients (see, for example, Hansson L et al.: *Effect of angiotensin-converting-enzyme inhibition compared with conventional therapy on cardiovascular morbidity and mortality in hypertension*: the Captoril Prevention Project (CAPPP) randomized trial, Lancet 353:611, 1999; Yusuf S et al.; *Effect of angiotensin-converting-enzyme inhibitor, ramipuril, on cardiovascular events in high-risk patients*: The Heart Outcome Prevention Evaluation Study Investigators, N. Engl J Med 342:145, 2000). Its mechanism of action is to cause an increase in sensitivity to insulin, i.e. the reduced action of insulin resistance has been suggested (see, for example, Tetsuya Shinai, Masatsugu Horiuchi, *Angiotensin and Diabetic Complications*, Gendai Iyaku (Modern Medicines), Vol. 35 No. 9, (2003)).

It is said that there are approximately 14 million diabetic patients including potential patients, and about 40% are presumed to be receiving medical drug therapy. However, in the case of medical drug therapy, adverse effects are of concern. The tremendous cost of medical drug therapy is also a problem in view of medical economics.

It is therefore desirable for patients with mild diabetes or potential patients about to develop diabetes to utilize effective supplement food (processed food) etc., if available, without receiving any medical drug therapy.

However, currently commercially available processed foods of onion extract such as those seen in Japanese Patent Laid-Open No. 10-77232 have not been satisfactory with respect to their effect.

The present inventors discovered that squash extract mixed with onion extract has excellent ACE inhibitory activity (described later in Examples 1 to 3), and therefore have filed an application entitled, "*Supplementary Foods Effective In Reducing Blood Pressure*" (Japanese Patent Application No. 2002-312459). As mentioned above, since the hypotensive effect based on ACE inhibitory activity also suppresses new onset diabetes, it is expected that supplement foods containing squash extract mixed with onion extract will have an anti-diabetic effect as well as the hypotensive effect. When these supplement foods were administered to diabetic patients with hypertension complications, extremely good performance as described later was obtained.

Supplement foods containing squash extract mixed with onion extract may not only be used as supplement foods (processed foods), but also as pharmaceuticals.

The object of the present invention therefore is to provide more effective supplement foods and safe pharmaceuticals with no adverse effects by means of both the hypotensive effect and anti-diabetic effect.

SUMMARY OF THE INVENTION

In order to accomplish the objective, the supplement food of the present invention comprises squash extract mixed with onion extract.

Further, the pharmaceutical of the present invention comprises squash extract mixed with onion extract.

Both squash and onion have been consumed by human beings for the past few thousand years as foodstuff. Their safety can well be presumed from this abundant experience in consuming, and they are available as raw material at low costs.

In addition, as they have been consumed for a long time and their safety is empirically proven as described above, by mixing squash extract powder with onion extract powder, then adding pharmaceutically acceptable additives (for example excipients, surfactants, etc.) as required, safe pharmaceuticals without adverse effects can be prepared.

By mixing squash extract with onion extract, a synergistic effect of the two extracts is expected, thus providing, for example, supplement foods and pharmaceuticals with combined hypotensive and anti-diabetic effects, which are safe and more effective than onion extract, etc. alone, and have no adverse effects.

BRIEF DESCRIPTION OF THE DRAWINGS

FIG. 2 shows the changes of substances related to elevation in blood pressure and hypotensive minerals after the ingestion of the products mixed with squash extract and onion extract;

FIG. 3 shows the correlation between systolic blood pressure and substances related to elevation in blood pressure; and FIG. 4 shows the changes of 2 hour postprandial blood glucose levels and $HbA_{1c}$ after the ingestion of the products mixed with squash extract and onion extract.

DETAILED DESCRIPTION OF THE PREFERRED EMBODIMENTS

Figure 1:
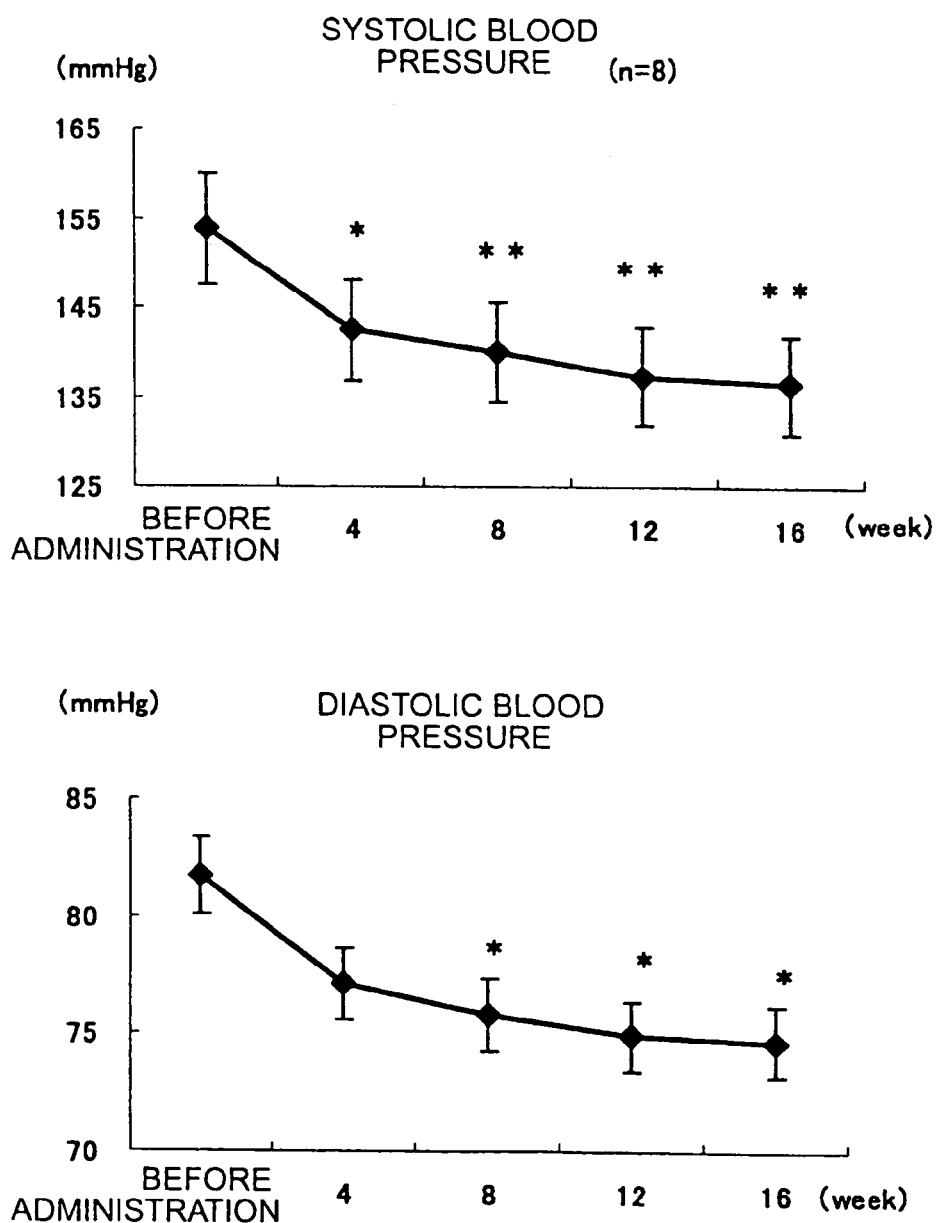
FIG. 1 shows the changes of systolic and diastolic blood pressure after the ingestion of the products mixed with squash extract and onion extract.

Preparation examples and samples will now be described.

PREPARATION EXAMPLE 1

Process for Preparing Squash Extract (Preprocess)

First, 78 kg of squash (cultivar Ebisu) was washed with Jet Washer (Arimitsu Industry Co., Ltd., SKY-130II) to remove surface soil, then peeled and deseeded by hand to obtain flesh. The flesh was grinded into a size of few millimeters with a Feather Mill (Hosokawa Micron Corporation, FM-65042) to obtain 56 kg of ground product.

(Preparation of Squeezed Liquid)

An equivalent amount of boiling water was prepared in a double-bottom pot, and then the ground product was added to the pot and the mixture was left at 90° C. for 10 minutes. The mixture was placed in a bag of filter fabric and squeezed with oil hydraulic press (Komagata Kikai Seisakusho, KS-3) to obtain 90 kg of squeezed liquid. Soluble solid matter content of this liquid was 5.4%.

(Preparation of Concentrated Liquid)

To reduce viscosity, 0.01% by weight of enzyme (Sankyo Co., Ltd., Sucrase N) was added to the squeezed liquid, and the mixture was left at 45° C. for 1 hour and then heated to 90° C. to inactivate the enzyme completely. This liquid was vacuum concentrated under conditions of a heating temperature of 120° C., 160mmHg, using a concentration pot (Yashima Chemical Engineering Co., Ltd., Type AS) to obtain 13 kg of concentrated liquid. Soluble solid matter content of this liquid was 36%.

(Preparation of Powder)

Food grade dextrin (Nissi Co., Ltd., NSD 500) 14 kg was dissolved in 28 kg of hot water, then heated at 95° C. for 20 minutes. The obtained concentrated liquid (13 kg) was added and the mixture was stirred to homogenize at 70 ° C. until uniform. Then, this was converted into powder using a spray drier (Ohkawara Kakohki Co., Ltd., Type L-12) under conditions of a blower temperature 150° C. and exhauster temperature 70° C., sievedwith 30-mesh to obtain 17.5 kg of squash extract powder.

Preparation Example 2

Process for Preparing Onion Extract

Ten kg of onions from Hokkaido were washed twice with water, then immediately put in a pot and heated to boil at 100° C. The boiled onions obtained were ground in a feather mill and squeezed with a squeezing apparatus to obtain 9.5 kg of squeezed liquid. Vacuum concentration was carried out using a heating temperature of 92° C., evaporation temperature of 42° C., and pressure of 15 mmHg using a centrifugal-film vacuum concentrator to obtain 0.9 kg of concentrated extract. The constituents distilled off during the vacuum concentration were passed through an activated charcoal layer to be adsorbed thereon. The adsorbed material was eluted with ethanol, and then the ethanol was removed from the solution by evaporation to obtain 1.5 g of residual component. This was added uniformly to the concentrated extract obtained earlier to obtain 0.9 kg of onion extract.

EXAMPLE 1

Results of Study of ACE Inhibitory Activity and Interaction between Squash and Onion Extracts Measurements were carried out according to the following partly modified Cushman & Cheung's method [*Seikagaku Jikkenhou 38: Shokuhinchu no Seitaikinou Chosetsubusshitsu Kenkyuhou* (Experimental Methods in Biochemistry 38: Methods of Researching Substances Regulating Vital Functions in Food Materials), Shunro Kawagishi ed., Gakkai Shuppan Center (1996)].

[Samples]
1) Squash extract (Nippon Shinyaku Co. Ltd., Chitose Foodstuffs Plant)
2) Onion extract (Nippon Shinyaku Co. Ltd., Chitose Foodstuffs Plant)
3) Commercially available food product A (specified health food containing lactotripeptide)
4) Commercially available food product B (specified heath food containing sardine peptide)

[Method]

1. Reagents
(1) Buffer: 450 ml of 50 mM $Na_2B_4O_7$ and 550 ml of 200 mM $H_3BO_3$ are mixed and adjusted to pH 8.3.
(2) Substrate solution: 7.6 mM Hip-His-Leu and 608 mM NaCl are dissolved in this buffer solution.
(3) ACE solution: ACE is dissolved in the above buffer (60 mU/ml of activity).

2. Method of Measurement
(1) 30 μl of a sample solution and 250 μl of a substrate solution are placed in a test tube, and then incubated in a thermobath at 37° C. for 5 minutes.
(2) 100 μl of ACE solution (6 mU) is added, immediately stirred, followed by reaction at 37° C. for 30 minutes.
(3) 250 μl of 1 N hydrochloric acid is added and stirred to terminate the reaction. 1.5 ml of ethyl acetate is added, stirred well, followed by extraction of hippurate released.
(4) Following centrifugation at 3000 rpm for 10 minutes, 0.5 ml of an ethyl acetate upper layer is recovered and put in a test tube.
(5) Ethyl acetate is aspirated and removed in a desiccator. After confirming the complete removal of ethyl acetate, 4 ml of distilled water is added and stirred well to dissolve the hippurate, and absorbance is measured at 228 nm.
(6) Inhibition rate is represented by:

$$\text{Inhibition}(\%) = \frac{Ec - Es}{Ec - EB} \times 100$$

Wherein Es is an absorbance when sample solution is added, Ec is an absorbance when distilled water instead of a sample solution is added, and EB is an absorbance when reacted after adding 1 N hydrochloric acid.

3. Calculation of Inhibitory Activity

The concentration of the sample in a reaction solution when an inhibition rate is 50% is defined as the IC50 value. Glucose contents of all samples are adjusted to 2.0° Bx before measurement.

[Results]

1) Single Materials

| Sample | Squash extract (Bx2.0) | Onion extract (Bx2.0) | Commercially available food product A | commercially available food product B |
|---|---|---|---|---|
| ACE inhibitory activity $IC_{50}$ (μl/ml) | 23.7 | 21.1 | 79.0 | 28.9 |

2) Mixture of Equal Amounts

| Sample | Squash extract + onion extract (each Bx2.0) | Commercially available food product A + onion extract | Commercially available food product B + onion extract |
|---|---|---|---|
| ACE inhibitory activity $IC_{50}$ (μl/ml) | 10.5 | 40.2 | 25.0 |

[Discussion]
1) Considerably high ACE inhibitory activity was seen with both of the squash extract alone and the onion extract alone.
2) The activities of leading products known to be specified health foods (commercially available food product A and commercially available food produce B) are as shown above; they showed lower activities than the squash extract alone and the onion extract alone.
3) In the case of squash extract+onion extract, a synergistic effect was notably seen; ACE inhibitory activity was prone to increase by 2-fold.
4) In the cases of commercially available food product A+onion extract and commercially available food product B+onion extract, no synergistic effect was seen (additive effect).
5) As can be considered from comparison to commercially available food products A and B, the amount of ingestion per day for squash extract appears to be approximately 3 to 10 g as powder containing 30% extract solid matter.

EXAMPLE 2

Clinical Study of Effects of the Products containing Squash Extract Mixed With Onion Extract on Hypotensive and Hypoglycemic Actions in Diabetic Patients With Hypertensive Complications (Yoshimi Saitou, Head Surgeon, Bunkyo Daiichi Iin)

Object

We have already confirmed the hypotensive effect of products containing squash extract mixed with onion extract, although its hypoglycemic effect in diabetic patients has not yet been studied. Hypoglycemic effect of onion extract alone has already been confirmed, although hypoglycemic effect when mixed with extract of squash extract has not yet been studied. The object of the present test is to examine the hypoglycemic effect of the products containing squash extract mixed with onion extract, compared with onion extract alone.

Methods

Subjects were 8 diabetic patients with hypertensive complications (3 males, 51, 59, and 70 years old; 5 females, 51, 61, 65, 68, and 70 years old). Three patients received hypotensive agents (calcium antagonists) concomitantly and 5 patients took no concomitant drugs. Seven patients received concomitant anti-diabetic drugs and 1 patient received no concomitant drugs. The 20 pills of products containing squash extract mixed with onion extract were ingested divided into 2 portions, 10 pills each, every morning and night. The observation period was set at 16 weeks, and the patients were followed before the intake and every 4 weeks after wards. Items examined were: Measurement of blood pressure, every 4 weeks (time of measurement was unified to either a.m. or p.m.); measurement of substances related to elevation of blood pressure (aldosterone, ACE, angiotensin II), before the intake and 8 and 16 weeks after the intake for a total of 3 measurements; measurement of hypotensive minerals (K, Ca, Mg), before the intake and 8 and 16 weeks after the intake for a total of 3 measurements; and measurement of blood glucose and $Hb_{A1C}$, every 4 weeks.

Results

The changes of systolic and diastolic blood pressure are shown in FIG. 1. Systolic and diastolic blood pressure decreased significantly at 4 weeks after beginning administration with the products containing squash extract mixed with onion extract, and subsequently gradually decreased. When observed case by case, the hypotensive effect was prone to be more significant when the pressure before beginning the administration was higher. Concomitant use of hypotensive agents did not seem to be correlated with the effect of the present product. Among substances related to elevation of blood pressure, angiotensin II and ACE were prone to decrease over time, and aldosterone showed virtually no change (FIG. 2). Hypotensive minerals Ca, K, and Mg also showed virtually no change (FIG. 2). As a result of examining correlation between systolic blood pressure and the substances related to elevation in blood pressure, there was a positive correlation between systolic blood pressure and ACE. That is, ACE decreased with decrease in blood pressure (FIG. 3). Similar trend was seen between diastolic blood pressure and ACE. The changes of postprandial blood glucose level are shown in FIG. 4. There was clearly a decrease in postprandial blood glucose level after beginning the administration, and statistically significant decrease was seen after 8 weeks. $Hb_{A1C}$ tended to decrease.

Discussion

It is hypothesized that the products mixed with squash extract and onion extract suppress ACE, and as a result suppress the production of angiotensin II, thus enhancing the hypotensive effect. It should be particularly noted that better postprandial hypoglycemic effect was seen, compared to onion extract alone as previously reported by us. From this fact, it can be hypothesized that squash extract also lowers blood glucose levels. Recently, hypotensive agents (ACE inhibitors) such as CAPTOPRIL® are reported to suppress the onset in diabetic patients and to suppress diabetic complications. The relationship between ACE inhibitor effect and reduced insulin resistance effect is being considered, and the action mechanism of squash extract in terms of hypoglycemic effect is thought to be due to insulin resistance reducing effect based on the ACE inhibitory effect of squash extract.

CONCLUSION

The products containing squash extract mixed with onion extract were proved to have hypotensive effect, as well as hypoglycemic effect stronger than that seen with onion extract alone. This mechanism of action was presumed to be from the insulin resistance reduction effect based on the ACE inhibitory effect of squash.

What is claimed is:
1. A food supplement comprising squash extract mixed with onion extract, wherein the food supplement is effective both in terms of a hypotensive effect and an anti-diabetic effect; and
wherein the squash extract is produced by a process comprising the steps of:
grinding squash flesh;
mixing the ground squash flesh with water;
squeezing the ground squash flesh with water through a filter to form a squeezed liquid;
adding an enzyme to the squeezed liquid;
vacuum concentrating the squeezed liquid to obtain a first concentrated liquid;
dissolving a dextrin in water to form a dextrin and water mixture and adding the first concentrated liquid to the dextrin and water mixture to form a second concentrate; and
drying the second concentrate; and wherein the onion extract is produced by a process comprising the steps of:
boiling onion to form a boiled onion;
grinding the boiled onion;
squeezing the ground, boiled onion to obtain a squeezed liquid; and
vacuum concentrating the squeezed liquid.

2. A pharmaceutical comprising squash extract mixed with onion extract, wherein the pharmaceutical is effective both in terms of a hypotensive effect and an anti-diabetic effect; and
wherein the squash extract is produced by a process comprising the steps of:
grinding squash flesh;
mixing the ground squash flesh with water;
squeezing the ground squash flesh with water through a filter to form a squeezed liquid;
adding an enzyme to the squeezed liquid;
vacuum concentrating the squeezed liquid to obtain a first concentrated liquid;
dissolving a dextrin in water to form a dextrin and water mixture and adding the first concentrated liquid to the dextrin and water mixture to form a second concentrate; and
drying the second concentrate; and
wherein the onion extract is produced by a process comprising the steps of:
boiling onion to form a boiled onion;
grinding the boiled onion;
squeezing the ground, boiled onion to obtain a squeezed liquid; and
vacuum concentrating the squeezed liquid.

* * * * *

UNITED STATES PATENT AND TRADEMARK OFFICE
CERTIFICATE OF CORRECTION

| | | |
|---|---|---|
| PATENT NO. | : 7,122,213 B2 | Page 1 of 1 |
| APPLICATION NO. | : 10/978718 | |
| DATED | : October 17, 2006 | |
| INVENTOR(S) | : Takahiko Anno et al. | |

It is certified that error appears in the above-identified patent and that said Letters Patent is hereby corrected as shown below:

Column 1, line 14;
"*Hyperglycemiain*" should be --*Hyperglycemia in*--.

Column 3, line 28;
"sievedwith" should be --sieved with--.

Signed and Sealed this

Third Day of June, 2008

JON W. DUDAS
*Director of the United States Patent and Trademark Office*